(12) United States Patent
Koski et al.

(10) Patent No.: US 10,973,494 B2
(45) Date of Patent: Apr. 13, 2021

(54) FLEXIBLE CIRCUIT WITH REDUNDANT CONNECTION POINTS FOR ULTRASOUND ARRAY

(71) Applicant: EchoNous, Inc., Redmond, WA (US)

(72) Inventors: Kelly James Koski, Bothell, WA (US); Joel Dean Wetzstein, Mountlake Terrace, WA (US); Greg Nieminen, Bothell, WA (US)

(73) Assignee: EchoNous, Inc., Redmond, WA (US)

( * ) Notice: Subject to any disclaimer, the term of this patent is extended or adjusted under 35 U.S.C. 154(b) by 312 days.

(21) Appl. No.: 15/699,771

(22) Filed: Sep. 8, 2017

(65) Prior Publication Data

US 2018/0070920 A1    Mar. 15, 2018

Related U.S. Application Data

(60) Provisional application No. 62/385,806, filed on Sep. 9, 2016.

(51) Int. Cl.
| | |
|---|---|
| *A61B 8/00* | (2006.01) |
| *H01L 41/311* | (2013.01) |
| *H01L 41/338* | (2013.01) |
| *B06B 1/06* | (2006.01) |
| *H01L 41/29* | (2013.01) |
| *H01L 41/047* | (2006.01) |
| *H05K 1/18* | (2006.01) |
| *B06B 1/02* | (2006.01) |

(Continued)

(52) U.S. Cl.
CPC .......... *A61B 8/4483* (2013.01); *B06B 1/0215* (2013.01); *B06B 1/0622* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 6,396,199 B1 * | 5/2002 | Douglas | ................ B06B 1/0622 |
| | | | 310/334 |
| 6,894,425 B1 | 5/2005 | Solomon et al. | |

(Continued)

FOREIGN PATENT DOCUMENTS

| | | |
|---|---|---|
| CN | 101361664 A | 2/2009 |
| CN | 105358070 A | 2/2016 |

(Continued)

OTHER PUBLICATIONS

International Search Report of the International Searching Authority, dated Dec. 15, 2017, for International Application No. PCT/US2017/050768, 3 pages.

*Primary Examiner* — Bryan P Gordon
(74) *Attorney, Agent, or Firm* — Seed Intellectual Property Law Group LLP

(57) ABSTRACT

Flex circuits and methods for ultrasound transducers are provided herein. In at least one embodiment, an ultrasound device includes a plurality of transducer elements and a flex circuit. The flex circuit includes an insulating layer having a first surface and a second surface opposite the first surface. A plurality of first conductive pads is included on the first surface of the insulating layer, and each of the first conductive pads is electrically coupled to a respective transducer element. A plurality of second conductive pads are included on the second surface of the insulating layer, and each of the second conductive pads is electrically coupled to a respective first conductive pad and the respective transducer element.

17 Claims, 3 Drawing Sheets

(51) Int. Cl.
 *H05K 1/11* (2006.01)
 *H04R 17/00* (2006.01)
(52) U.S. Cl.
 CPC .......... *H01L 41/0475* (2013.01); *H01L 41/29* (2013.01); *H01L 41/311* (2013.01); *H01L 41/338* (2013.01); *H05K 1/112* (2013.01); *H05K 1/189* (2013.01); *B06B 2201/20* (2013.01); *H04R 17/005* (2013.01); *H05K 2201/0154* (2013.01); *H05K 2201/10151* (2013.01)

(56) References Cited

U.S. PATENT DOCUMENTS

| | | | |
|---|---|---|---|
| 2001/0041837 A1* | 11/2001 | Takeuchi | H01L 41/37 600/437 |
| 2008/0178677 A1 | 7/2008 | Baumgartner et al. | |
| 2008/0315331 A1 | 12/2008 | Wodnicki et al. | |
| 2009/0034370 A1* | 2/2009 | Guo | H04R 31/00 367/180 |
| 2013/0257226 A1 | 10/2013 | Nobles et al. | |
| 2014/0375171 A1 | 12/2014 | Tai | |
| 2015/0266058 A1* | 9/2015 | Yoshida | B06B 1/0622 600/443 |
| 2016/0007964 A1* | 1/2016 | Ona | G01S 15/8927 600/459 |
| 2016/0126445 A1* | 5/2016 | Kiyose | H01L 41/0533 310/316.01 |

FOREIGN PATENT DOCUMENTS

| | | |
|---|---|---|
| KR | 10-1151844 B1 | 6/2012 |
| RU | 2 418 384 C2 | 5/2011 |
| WO | 01/03108 A2 | 1/2001 |

\* cited by examiner

FLEXIBLE CIRCUIT WITH REDUNDANT CONNECTION POINTS FOR ULTRASOUND ARRAY

BACKGROUND

Technical Field

The present application pertains to ultrasound systems, and more particularly to ultrasound systems including a flex circuit for attachment to ultrasound transducer elements in an acoustic stack.

Description of the Related Art

Ultrasonic transducers generally include piezoelectric transducer elements, which are electrically connected to circuitry such as driving or receiving circuitry for driving the transmission of an ultrasound signal (e.g., an ultrasound pulse) and/or for receiving a reflected ultrasound signal (e.g., an echo signal). The transducer elements are coupled to a flex circuit, which provides signal lines for transmitting signals between the transducer elements and the driving circuitry, receiving circuitry, processing circuitry or the like. Such circuitry is typically included in electronic equipment that is positioned external to the ultrasound probe, such as an equipment cart or a handheld computing device. The flex circuit thus couples the transducer elements to the processing, driving and/or receiving circuitry.

During operation, an electrical pulse is applied to electrodes of the transducer elements, which causes a mechanical change in dimension of the transducer elements and generates an acoustic wave that is transmitted toward a target structure of interest, e.g., an organ or other physiological feature within a patient's body. The transmitted acoustic wave is then reflected from the target structure of interest and is received at the surface of the transducer elements, which in response generate a voltage that is detectable as a receive signal by the associated processing and/or receiving circuitry.

Ultrasonic transducers may include transducer elements that are arranged as phased arrays having one or more rows of transducer elements that are electrically and acoustically isolated from one another. Such arrays may include 64 or more individual transducer elements. An acoustic stack may be formed, including such transducer elements, as a layered structure including a backing layer, a flex circuit, the transducer elements (e.g., piezoelectric ceramic elements), and an acoustic matching layer. The flex circuit typically includes conductive traces formed on one side of an insulating layer. The conductive traces are then coupled to respective transducer elements.

An important feature of an ultrasound array, and of the design of such an array, is the reliability of the signal pulse path to and from the transducer elements in the array. If there is a short circuit, open circuit, high resistance, or any defect in the signal path, the signals provided to and from the connected transducer elements may not produce reliable information from which an ultrasound image can accurately be formed.

The point at which the conductive traces of the flex circuit are coupled to respective transducer elements is thus a critical coupling point, as all driving signals to be provided from the driving circuitry to the transducer elements are provided through the individual conductive traces. Similarly, received echo signals may be provided from the transducer elements to the receiving and/or processing circuitry through the individual conductive traces coupled to the transducer elements.

BRIEF SUMMARY

The present disclosure, in part, addresses a desire for better signal path continuity through a flex circuit in an ultrasound transducer. Improving signal path continuity through the flex circuit results in more reliable signal communication between the processing, driving and/or receiving circuitry and the transducer elements.

Embodiments provided by the present disclosure improve signal communication through a flex circuit by providing redundant connection points for transmitting a signal to each transducer element in the ultrasound transducer, e.g., in the acoustic stack of the ultrasound transducer. Redundant connection points may be provided by including conductive pads on both sides of an insulating layer of the flex circuit. The conductive pads on one side of the insulating layer are coupled to respective conductive traces formed on the same side of the insulating layer. Further, conductive pads are formed on an opposite side of the insulating layer, and corresponding conductive pads on opposite sides of the insulating layer are aligned with one another and coupled to one another by conductive vias formed through the insulating layer. Accordingly, even if a defect exists in the attachment point of one of the conductive pads to a transducer element (which defect may cause, for example, an open circuit, high resistance, or the like), signals may still be reliably provided to and from the transducer element through a second electrical connection point provided by the conductive pad formed on the opposite side of the insulating layer.

In at least one embodiment, an ultrasound transducer is provided that includes a plurality of transducer elements and a flex circuit. The flex circuit includes an insulating layer having a first surface and a second surface opposite the first surface. A plurality of first conductive pads is formed on the first surface of the insulating layer, and each first conductive pad is electrically coupled to a respective transducer element. A plurality of second conductive pads is formed on the second surface of the insulating layer, and each of the second conductive pads is electrically coupled to a respective first conductive pad and the respective transducer element.

In another embodiment, an ultrasound transducer is provided that includes a flex circuit. The flex circuit includes an insulating layer having a first surface and a second surface opposite the first surface, a plurality of conductive traces on the first surface of the insulating layer that are each electrically coupled to respective first conductive pads on the first surface of the insulating layer, and a plurality of second conductive pads on the second surface of the insulating layer. The flex circuit further includes a plurality of conductive vias, each of which extend through a respective first conductive pad, the insulating layer, and a respective second conductive pad. Each of the conductive vias electrically couple respective first and second conductive pads to each another. The ultrasound transducer may further include a plurality of transducer elements, with each of the transducer elements being electrically coupled to a respective first conductive pad and a respective second conductive pad.

In yet another embodiment, a method is provided that includes forming a plurality of conductive traces on a first surface of an insulating layer; forming a plurality of first conductive pads on the first surface of the insulating layer, each of the first conductive traces being electrically coupled to a respective first conductive pad; forming a plurality of second conductive pads on a second surface of the insulating layer, the second surface being opposite the first surface; and electrically coupling each of the first conductive pads to a respective second conductive pad.

DETAILED DESCRIPTION

In various embodiments described herein, a flex circuit for an ultrasound transducer may include conductive pads formed on each of two opposite sides of an insulating layer of the flex circuit. The conductive pads on a first side of the insulating layer are respectively electrically coupled to corresponding conductive pads on a second side of the insulating layer by a conductive via formed through the corresponding conductive pads and the insulating layer. The conductive pads on one of the first side or the second side of the insulating layer are electrically coupled to respective conductive traces on the flex circuit. The flex circuit may be coupled to an acoustic stack such that each transducer element in the acoustic stack is electrically coupled to at least two conductive pads, i.e., conductive pads on opposite sides of the insulating layer that are electrically coupled to each other by a conductive via. The flex circuit thus provides at least two points of contact, provided by each of the conductive pads coupled to one another through the conductive via, through which a signal transmitted along a conductive trace (e.g., a driving signal for driving a connected transducer element to transmit an ultrasound pulse or an echo signal received by a connected transducer element) may be provided to or received from a transducer element.

Figure 1:
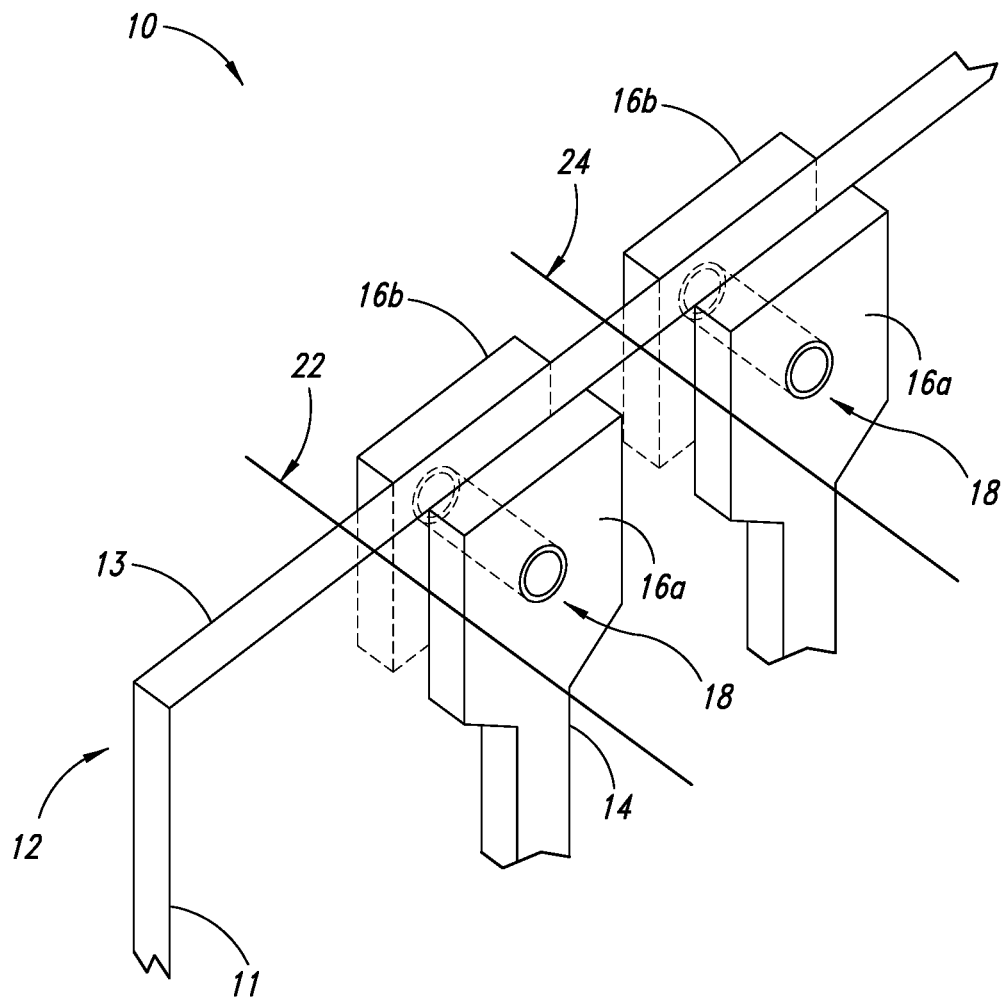
FIG. 1 is a perspective view of a flex circuit for an acoustic stack in an ultrasound transducer, in accordance with one or more embodiments of the present disclosure.

FIG. 1 is a perspective view of at least one embodiment of a flex circuit 10 for an acoustic stack in an ultrasound transducer. The flex circuit 10 includes an insulating layer 12, conductive traces 14, and conductive pads 16.

The insulating layer 12 is made of any suitable flexible insulating material, such as polyimide. Conductive traces 14 are formed on a first surface 11 (e.g., a front surface) of the insulating layer 12. The conductive traces 14 may be made of any conductive material and may be formed using any suitable process, such as by deposition of the conductive material on the insulating layer 12 using one or more masks or deposition patterns. In one or more embodiments, the conductive traces 14 include copper.

Each of the conductive traces 14 formed on the first surface 11 of the insulating layer 12 is coupled to a respective conductive pad 16a on the first surface 11. The conductive pads 16a may be formed in a same process, and of a same material, as the conductive traces 14.

In the embodiment shown in FIG. 1, each of the conductive pads 16a on the first surface 11 of the insulating layer 12 is aligned with, and electrically coupled to, a respective conductive pad 16b that is formed on a second surface 13 (e.g., a back surface) of the insulating layer 12. The conductive pads 16a, 16b are electrically coupled to one another by a conductive through-hole or via 18.

The via 18 is formed through the aligned, corresponding conductive pads 16a on the first surface 11 and conductive pads 16b on the second surface 13. A through-hole may be formed, for example, by drilling, punching or the like through the aligned conductive pads 16a, 16b on the first and second surfaces 11, 13 of the insulating layer 12, and the through-hole may then be plated with a conductive material, such as copper. As such, the vias 18 electrically couple respective conductive pads 16a, 16b through the insulating layer 12. Accordingly, a signal provided through a trace 14 on the first surface 11 of the insulating layer 12 is provided to a conductive pad 16a on the first surface 11, as well as to a corresponding conductive pad 16b on the second surface 13, through the via 18.

The flex circuit 10 thus provides redundant points of electrical contact when attached to an acoustic stack. That is, the flex circuit 10 may be attached to the acoustic stack such that corresponding conductive pads 16a, 16b formed on each side of the insulating layer 12 are each in contact with a respective transducer element in the acoustic stack. Additionally, since the corresponding conductive pads 16a, 16b are electrically coupled to one another by the conductive via 18, a signal provided through a trace 14 on the first surface 11 of the insulating layer 12 will be transmitted to the respective transducer element by the corresponding conductive pads on both surfaces 11, 13 of the insulating layer 12. Accordingly, transmission of a signal (e.g., a driving signal) to a transducer element in an acoustic stack may be facilitated even in the event, for example, that one of the corresponding conductive pads 16a, 16b has a faulty connection with the transducer element or is in any way deteriorated in its ability to carry an electrical signal.

The flex circuit 10 may be diced into individual conductive paths using, for example, a dicing saw. The flex circuit 10 may be diced so that each of the conductive paths includes a respective conductive trace 14 and corresponding conductive pads 16a, 16b formed on respective surfaces of the insulating layer 12. The flex circuit 10 may be cut, for example, along dicing lines 22, 24, as shown in FIG. 1.

Figure 2:
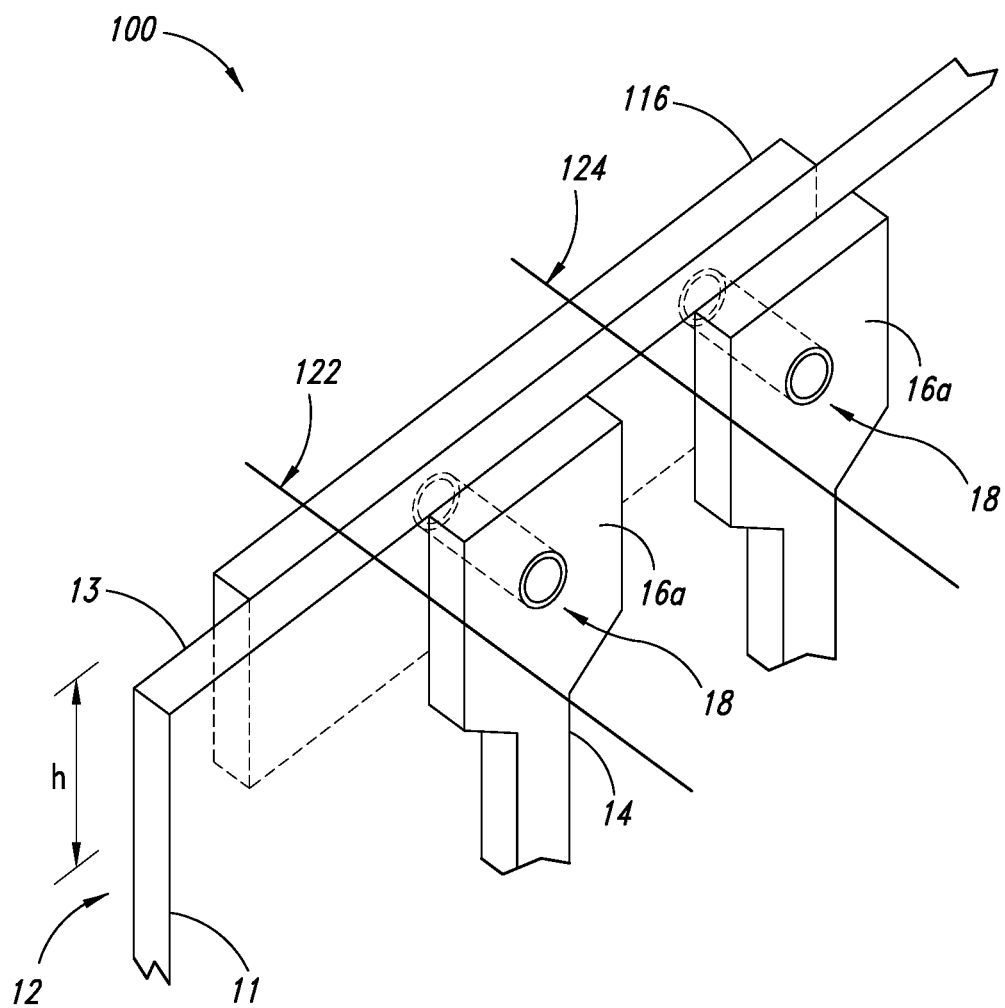
FIG. 2 is perspective view of another flex circuit for an acoustic stack in an ultrasound transducer, in accordance with one or more embodiments of the present disclosure.

FIG. 2 is a perspective view of a flex circuit 100 in accordance with one or more alternative embodiments of the present disclosure. The flex circuit 100 of FIG. 2 is similar in structure and in function to the flex circuit 10 of FIG. 1, except for the differences that will be discussed below. The features shared by the flex circuits 10 and 100 will not be described here again in the interest of brevity.

The main difference between the flex circuits 10 and 100 is that, in the flex circuit 100 of FIG. 2, conductive pads on the second surface 13 of the insulating layer 12 are formed from a single conductive bus 116. The conductive bus 116 may be formed, for example, of copper using a deposition technique. Alternatively, the conductive bus 116 may be a prefabricated piece of conductive material that is bonded to the second surface 13 of the insulating layer 12 using, for example, an adhesive. In one or more embodiments, the conductive bus 116 has a height (h) of about 5 millimeters. The conductive bus 116 is formed on or bonded to an opposite surface of the insulating layer 12 (e.g., the second surface 13, as shown) as the conductive pads 16a. As in the flex circuit 10 of FIG. 1, conductive vias 18 are formed through the conductive pads 16a on the first surface 11 of the insulating layer 12, thereby electrically coupling the conductive pads 16a to corresponding regions of the conductive bus 116 on the second surface 13 of the insulating layer 12.

The flex circuit 100 may then be diced into individual conductive paths using a dicing saw and cutting, for example, along dicing lines 122, 124. After dicing through the conductive bus 116 and the insulating layer 12, as shown at dicing lines 122, 124, the flex circuit 100 includes individual conductive paths made up of the traces 14 formed on the first surface 11 of the insulating layer, as well as conductive pads 16a on the first surface 11 and corresponding conductive regions of the conductive bus 116 on the second surface 13 (i.e., portions of the conductive bus 116 after dicing) that are coupled to respective conductive pads 16a through the conductive vias 18.

Figure 3A:
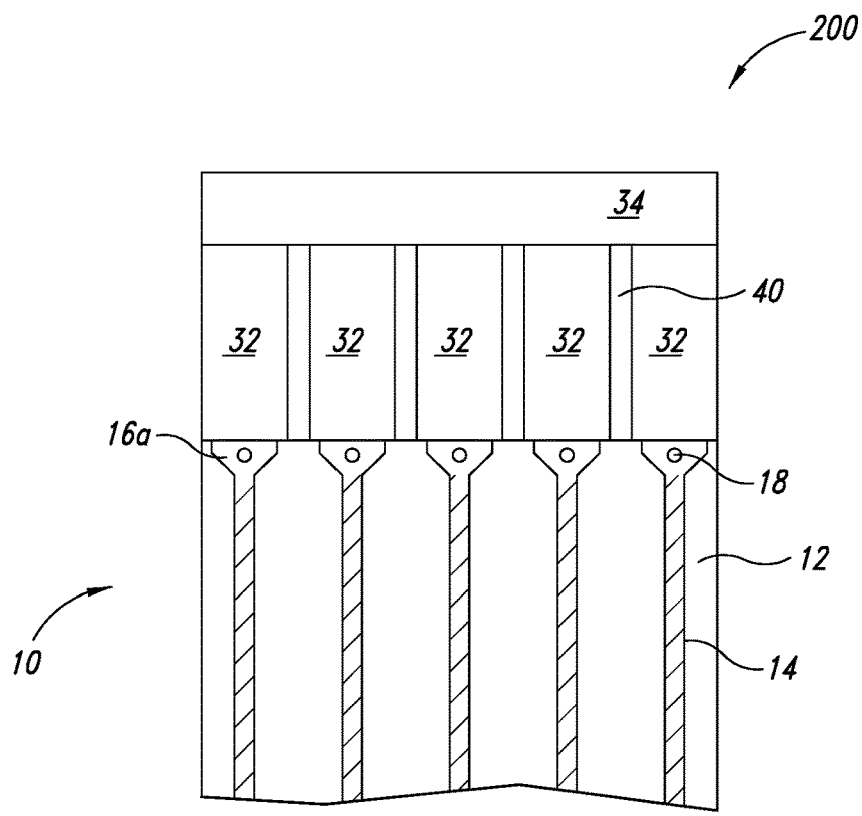
FIG. 3A is a front view illustrating an ultrasound transducer acoustic stack including a flex circuit in accordance with one or more embodiments of the present disclosure.
Figure 3B:
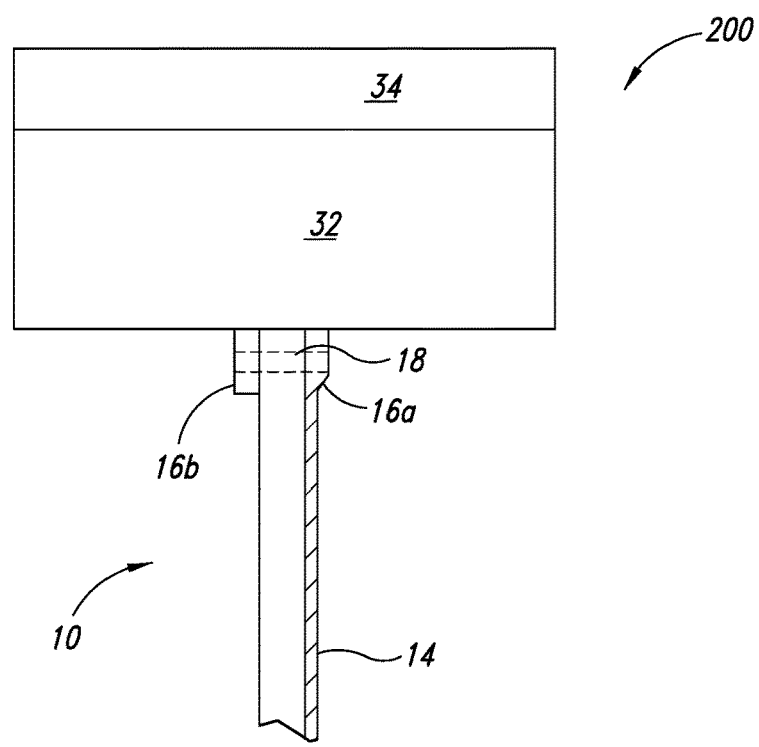
FIG. 3B is a side view of the acoustic stack shown in FIG. 3A, in accordance with one or more embodiments of the present disclosure.

FIG. 3A is a front view illustrating an ultrasound transducer acoustic stack 200 including a flex circuit in accordance with one or more embodiments of the present disclosure, and FIG. 3B is a side view of the acoustic stack 200 shown in FIG. 3A.

The acoustic stack 200 includes a plurality of transducer elements 32, an acoustic matching layer 34, and a flex circuit 10. The flex circuit 10 is attached to a lower surface of the transducer elements 32, and the acoustic matching layer 34 is attached to an upper surface of the transducer elements 32.

The flex circuit 10, transducer elements 32, and acoustic matching layer 34 may be attached to one another to form the acoustic stack 200 using an adhesive material, such as an epoxy. In one or more embodiments, the transducer elements 32 are made of a piezoelectric material, such as a piezoelectric ceramic material. The transducer elements 32 may include electrodes (e.g., signal electrodes and/or ground electrodes) which are electrically coupled to the conductive pads 16a, 16b formed on the first and second surfaces 11, 13, respectively, of the insulating layer 12. Alternatively, the transducer elements 32 may be electrically coupled to respective conductive pads 16a, 16b by attaching the transducer elements 32 to the flex circuit 10 with a conductive epoxy, solder, solder paste, or the like. The flex circuit 10 is attached to the transducer elements 32 in such a way that each transducer element 32 is electrically coupled to two conductive pads 16a, 16b, one on each surface 11, 13 of the insulating layer 12, thereby establishing redundant points of contact for transmitting a signal from the associated conductive trace 14 to the transducer element 32.

The acoustic block 200 shown in FIGS. 3A and 3B may be formed by a variety of fabrication processes. In one embodiment, the transducer elements 32 may be provided initially as a single block of piezoelectric material. Similarly, the conductive pads 16a on the first surface 11 of the insulating layer 12 and/or the conductive pads 16b on the second surface 13 of the insulating layer 13 may initially be provided as a block of conductive material (e.g., the conductive bus 116 shown in FIG. 2) electrically coupled to the respective traces 14 on the insulating layer 12.

Through-holes may be formed e.g., by drilling, punching or the like, through the conductive bus 116 on the second surface 13 at locations that will be included in the conductive pads 16b, once formed. The through-holes are formed to extend through the conductive bus 116, the insulating layer 12, and the conductive pads 16a on the first surface 11 of the insulating layer 12. The through-holes may then be plated or otherwise coated with a conductive material, such as copper, to form the conductive vias 18 which electrically couple the conductive pads 16a to associated regions of the conductive bus 116 that, after dicing, will become conductive pads 16b on the second surface 13 of the insulating layer 12.

The piezoelectric block may be attached to the flex circuit 10 such that the conductive pads 16a on the first surface 11 and the conductive bus 116 on the second surface 13 are in contact with the piezoelectric block. The piezoelectric block and the flex circuit 10 may then be diced into individual transducer elements 32 and corresponding conductive pads 16a, 16b using a dicing saw. As such, a plurality of individual transducer elements 32 may be formed, with each transducer element 32 being electrically coupled to a pair of associated conductive pads 16a, 16b of the flex circuit 10. Each of the conductive pads 16a is electrically coupled to a corresponding trace 14 formed on the first surface 11 of the insulating layer 12, and each conductive pad 16a is further coupled by a conductive via 18 to a respective conductive pad 16b on the second surface 13 of the insulating layer 12. Accordingly, a redundant electrical connection is formed between the flex circuit 10 and the transducer elements 32, as each trace 14 of the flex circuit 10 is coupled to a conductive pad 16a on the first surface 11 of the insulating layer 12, as well as to a conductive pad 16b on the second surface 13 of the insulating layer 12.

After the piezoelectric block has been diced into individual transducer elements 32, as described above, gaps formed between transducer elements 32 and/or between adjacent conductive pads 16a, 16b of the flex circuit 10 may be filled with an adhesive material, such as an epoxy filling 40.

The acoustic matching layer 34 may then be attached to an upper surface of the transducer elements 32 and/or epoxy filling 40 using any suitable adhesive, such as an epoxy.

The conductive pads 16a on the first surface 11 of the insulating layer 12 do not necessarily have the same dimensions as the corresponding conductive pads 16b on the second surface 13 of the insulating layer 12. For example, as shown in FIG. 2, the conductive pads 16b may be formed by dicing through the conductive bus 116, while the conductive pads 16a may be already formed of suitable dimensions, along with the traces 14. In such a case, the conductive pads 16b formed after dicing the flex circuit 10 may have a larger area dimension than the pre-formed conductive pads 16a.

In another embodiment, the transducer elements 32 may be initially provided as a single block of piezoelectric material, while the flex circuit 10 may have been previously cut into a plurality of traces 14 and associated conductive pads 16a, 16b with conductive vias 18 formed through corresponding conductive pads 16a, 16b. The pre-cut flex circuit 10 may be attached to the piezoelectric block such that each associated pair of conductive pads 16a, 16b contacts the piezoelectric block at regions that will later be cut into individual transducer elements 32. The piezoelectric block is then diced into individual transducer elements 32, for example, using a dicing saw.

In yet another embodiment, the acoustic stack 10 may be formed from transducer elements 32 that have already been diced, and from the flex circuit 10 that has also already been diced to form a plurality of traces 14 and associated conductive pads 16a, 16b with conductive vias 18 formed through corresponding conductive pads 16a, 16b. In such a case, the transducer elements 32 may be directly attached or otherwise electrically coupled to respective conductive pads 16a, 16b on the first and second surfaces 11, 13, respectively, of the insulating layer 12. The epoxy filling 40 may be applied, and the acoustic matching layer 34 may be attached to the transducer elements 32 as described herein.

The various features and elements of the embodiments described above can be combined in additional ways to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An ultrasound transducer, comprising:
   a plurality of transducer elements; and
   a flex circuit including:
      an insulating layer having a first surface and a second surface opposite the first surface;
      a plurality of first conductive pads on the first surface of the insulating layer, each of the first conductive pads being electrically coupled to and in contact with a respective transducer element;
      a plurality of conductive traces on the first surface of the insulating layer, each conductive trace being electrically coupled to a respective first conductive pad; and
      a plurality of second conductive pads on the second surface of the insulating layer, each of the plurality of second conductive pads being electrically coupled to a respective first conductive pad and further electrically coupled to and in contact with the respective transducer element with which the respective first conductive pad is electrically coupled and in contact,
      wherein each of the first and second conductive pads has a width that is greater than a width of the conductive traces, and
      wherein the first conductive pads are electrically coupled to respective second conductive pads by a conductive via formed through the respective first and second conductive pads.

2. The ultrasound transducer of claim 1 wherein the plurality of first conductive pads and the plurality of second conductive pads are respectively attached to the plurality of transducer elements.

3. The ultrasound transducer of claim 1, further comprising an acoustic matching layer positioned on and attached to the plurality of transducer elements.

4. The ultrasound transducer of claim 1 wherein the insulating layer includes polyimide.

5. An ultrasound transducer, comprising:
   a flex circuit including:
      an insulating layer having a first surface and a second surface opposite the first surface;
      a plurality of conductive traces on the first surface of the insulating layer, each of the conductive traces having a first width;
      a plurality of first conductive pads on the first surface of the insulating layer, each of the first conductive pads being electrically coupled to a respective conductive trace, each of the first conductive pads having a second width that is greater than the first width of the conductive traces;
      a plurality of second conductive pads on the second surface of the insulating layer; and
      a plurality of conductive vias, each of the conductive vias extending through a respective first conductive pad, the insulating layer, and a respective second conductive pad, each of the conductive vias electrically coupling the respective first and second conductive pads to each another; and a plurality of transducer elements, each of the transducer elements being electrically coupled to and in contact with a respective first conductive pad and a respective second conductive pad.

6. The ultrasound transducer of claim 5 wherein each of the transducer elements is attached to the respective first and second conductive pads.

7. The ultrasound transducer of claim 5, further comprising an acoustic matching layer positioned on and attached to the plurality of transducer elements.

8. The ultrasound transducer of claim 5 wherein the insulating layer includes polyimide.

9. A method, comprising:
   forming a plurality of conductive traces on a first surface of an insulating layer;
   forming a plurality of first conductive pads on the first surface of the insulating layer, each of the first conductive traces being electrically coupled to a respective first conductive pad, each of the first conductive pads having a first width greater than a width of the conductive traces;
   forming a plurality of second conductive pads on a second surface of the insulating layer, the second surface being opposite the first surface, each of the second conductive pads having a second width greater than the width of the conductive traces;
   electrically coupling each of the first conductive pads to a respective second conductive pad by forming a plurality of conductive vias, each of the conductive vias extending through a respective first conductive pad, the insulating layer, and a respective second conductive pad; and
   electrically coupling respective first and second conductive pads to a respective ultrasound transducer element, the respective first and second conductive pads being in contact with the respective ultrasound transducer element.

10. The method of claim 9 wherein forming the plurality of first conductive pads includes:
    attaching a conductive bus to the first surface of the insulating layer, each of the first conductive traces being coupled to a respective portion of the conductive bus; and
    dicing the conductive bus to form the plurality of first conductive pads.

11. The method of claim 9 wherein forming the plurality of second conductive pads includes:
    attaching a conductive bus to the second surface of the insulating layer; and
    dicing the conductive bus to form the plurality of second conductive pads.

12. The method of claim 9 wherein forming the plurality of first conductive pads includes attaching a first conductive bus to the first surface of the insulating layer and dicing the first conductive bus, and
    wherein forming the plurality of second conductive pads includes attaching a second conductive bus to the second surface of the insulating layer, and dicing the second conductive bus.

13. The method of claim 9, further comprising:
    forming an acoustic matching layer on the respective transducer element.

14. The method of claim 9, further comprising:
    attaching a block of piezoelectric material to the plurality of first conductive pads and to the plurality of second conductive pads; and dicing the block of piezoelectric material to form a plurality of ultrasound transducer elements.

15. The ultrasound transducer of claim 1 wherein the second conductive pads have a different shape than the first conductive pads.

16. The ultrasound transducer of claim 5 wherein each of the second conductive pads has a third width that is greater than the first width of the conductive traces.

17. The ultrasound transducer of claim 5 wherein the second conductive pads have a different shape than the first conductive pads.

* * * * *